(12) United States Patent
Asirvatham et al.

(10) Patent No.: US 11,219,772 B2
(45) Date of Patent: Jan. 11, 2022

(54) DEVICES AND METHODS FOR CARDIAC PACING AND RESYNCHRONTZATION

(71) Applicant: Mayo Foundation for Medical Education and Research, Rochester, MN (US)

(72) Inventors: Samuel J. Asirvatham, Rochester, MN (US); Paul A. Friedman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/758,178

(22) PCT Filed: Oct. 24, 2018

(86) PCT No.: PCT/US2018/057235
§ 371 (c)(1),
(2) Date: Apr. 22, 2020

(87) PCT Pub. No.: WO2019/084102
PCT Pub. Date: May 2, 2019

(65) Prior Publication Data
US 2020/0330780 A1    Oct. 22, 2020

Related U.S. Application Data

(60) Provisional application No. 62/577,016, filed on Oct. 25, 2017.

(51) Int. Cl.
*A61N 1/375* (2006.01)
*A61N 1/368* (2006.01)
*A61N 1/05* (2006.01)

(52) U.S. Cl.
CPC ....... *A61N 1/37512* (2017.08); *A61N 1/3684* (2013.01); *A61N 1/3756* (2013.01); *A61N 1/37518* (2017.08); *A61N 1/057* (2013.01)

(58) Field of Classification Search
None
See application file for complete search history.

(56) References Cited

U.S. PATENT DOCUMENTS

| | | | |
|---|---|---|---|
| 4,276,882 A | 7/1981 | Dickhudt et al. | |
| 4,919,135 A | 4/1990 | Phillips, Jr. et al. | |
| 6,144,879 A | 11/2000 | Gray | |

(Continued)

FOREIGN PATENT DOCUMENTS

| | | |
|---|---|---|
| WO | WO 2008/134755 | 11/2008 |
| WO | WO 2009/081396 | 7/2009 |

OTHER PUBLICATIONS

International Preliminary Report on Patentability in International Application No. PCT/US2018/057235 dated May 7, 2020, 7 pages.

(Continued)

*Primary Examiner* — Brian T Gedeon
(74) *Attorney, Agent, or Firm* — Fish & Richardson P.C.

(57) ABSTRACT

This document relates to methods and materials for improving artificial cardiac pacing and/or resynchronization. For example, this document relates to methods and devices for artificial cardiac pacing and/or resynchronization by stimulating the His bundle.

17 Claims, 3 Drawing Sheets

(56) References Cited

U.S. PATENT DOCUMENTS

| | | | |
|---|---|---|---|
| 7,389,134 B1* | 6/2008 | Karicherla | A61B 5/0215 |
| | | | 600/375 |
| 7,981,020 B2 | 7/2011 | Mortier et al. | |
| 8,267,951 B2 | 9/2012 | Whayne et al. | |
| 2007/0005114 A1* | 1/2007 | Salo | A61N 1/36521 |
| | | | 607/17 |
| 2007/0055091 A1 | 3/2007 | Lau et al. | |
| 2007/0203391 A1 | 8/2007 | Bloom et al. | |
| 2007/0233216 A1 | 10/2007 | Liu et al. | |
| 2008/0147157 A1 | 6/2008 | Sweeney et al. | |
| 2010/0004504 A1 | 1/2010 | Callas et al. | |
| 2013/0046356 A1 | 2/2013 | Jensen et al. | |
| 2014/0018874 A1 | 1/2014 | Zhu et al. | |
| 2014/0107405 A1 | 4/2014 | Hjelle et al. | |
| 2016/0228699 A1 | 8/2016 | Monteiro | |
| 2017/0105675 A1 | 4/2017 | Zhou et al. | |

OTHER PUBLICATIONS

International Search Report & Written Opinion in International Application No. PCT/US2018/057235 dated Jan. 11, 2019, 13 pages.

U.S. Appl. No. 16/647,062, filed Mar. 13, 2020, Samuel J. Asirvatham, Pending.

* cited by examiner

DEVICES AND METHODS FOR CARDIAC PACING AND RESYNCHRONTZATION

CROSS-REFERENCE TO RELATED APPLICATIONS

This application is a National Stage application under 35 U.S.C. § 371 of International Application No. PCT/US2018/057235, having an International Filing Date of Oct. 24, 2018, which claims priority to U.S. Application Ser. No. 62/577,016, filed on Oct. 25, 2017. The disclosures of the prior applications are considered part of the disclosure of this application, and are incorporated in their entirety into this application.

BACKGROUND

1. Technical Field

This document relates to methods and materials for improving artificial cardiac pacing and/or resynchronization. For example, this document relates to methods and devices for artificial cardiac pacing and/or resynchronization by stimulating the His bundle.

2. Background Information

A pacemaker system is a small, battery-operated device that senses when a heart is beating irregularly or too slowly. The pacemaker system can also generate and deliver pulse signals to the heart to induce the heart to beat at the correct pace.

The primary purpose of a pacemaker is to maintain an adequate heart rate, either because the heart's natural pacemaker is not fast enough, or because there is a block in the heart's electrical conduction system. Arrhythmias are problems with the rate or rhythm of the heartbeat. During an arrhythmia, the heart can beat too fast, too slow, or with an irregular rhythm.

Most conventional pacemakers have two parts. One part is the generator containing a battery and the electrical circuitry to control the heartbeat. Another part are one or more leads. Leads are wires that connect the heart to the generator and carry the electrical signals to and from the heart. The leads detect the heart's rhythm contractions and send corresponding signals to the controller of the generator. Also, the leads carry the pacing pulses from the generator to the myocardium.

Modern pacemakers are externally programmable and allow a cardiologist to select the optimum pacing modes for individual patients. Some combine a pacemaker and defibrillator in a single implantable device. Others have multiple electrodes stimulating differing positions within the heart to improve the atrioventricular synchronization of the heart.

SUMMARY

This document describes methods and devices for improving artificial cardiac pacing and/or resynchronization. For example, this document describes methods and devices for artificial cardiac pacing and/or resynchronization by stimulating the His bundle.

In one aspect, this disclosure is directed to a cardiac pacing device. The cardiac pacing device can include a first flange portion, a second flange portion, a central portion extending between and connecting the first flange portion and the second flange portion, and one or more pacing electrodes exposed on an inward-facing surface of the first flange portion that faces the second flange portion. In some cases, the pacing device can be secured without puncturing a conduction system of a heart. In some cases, the cardiac pacing device can include one or more pacing electrodes exposed on an inward-facing surface of the second flange portion that faces the first flange portion. In some cases, the cardiac pacing device can include a wireless receiver configured for wireless communication with a controller separated from the cardiac pacing device, and the controller can wirelessly communicate to the cardiac pacing device to control the cardiac pacing device. In some cases, the cardiac pacing device can include a controller circuitry coupled housed in the cardiac pacing device, and the cardiac pacing device can be a fully self-contained pacing device. In some cases, the cardiac pacing device can include one or more pressure sensors coupled to the cardiac pacing device and configured for detecting a fluid pressure adjacent the cardiac pacing device. In some cases, the first flange portion can be configured to be located within the myocardium of the heart, and the second flange portion is configured to be located on a right ventricular aspect. In some cases, the first flange portion can be configured to be located in a right ventricular outflow tract, and the second flange portion can be configured to be located just into a proximal right atrial appendage.

In another aspect, this disclosure is directed to a method of treating a human heart. The method can include inserting a sheath with a pacing device in the heart, where the sheath comprises an electrode, locating a conductive system of the heart via the electrode on the sheath, deploying the pacing device in the heart, and confirming, via the electrode on the sheath, function of the pacing device. In some cases, the pacing device can include a first flange portion, a second flange portion, a central portion extending between and connecting the first flange portion and the second flange portion, and one or more pacing electrodes exposed on an inward-facing surface of the first flange portion that faces the second flange portion. In some cases, the conductive system can be a His bundle of the heart. In some cases, locating the His bundle of the heart can include recording His bundle activity via the electrode on the sheath. In some cases, templates of the His bundle recording can be compared to the His bundle activity recorded via the electrode on the sheath to confirm location of the His bundle. In some cases, deploying the pacing device can include placing a distal portion of the pacing device within a myocardium of the heart, and placing a proximal portion on the myocardium on a right ventricular aspect of the heart. In some cases, deploying the pacing device can include placing a distal portion of the pacing device just distal to a crista supraventricularis of the heart in a proximal right ventricular outflow tract, and placing a proximal portion of the pacing device through a His bundle of the heart and is placed in a clamp-like manner into the proximal right atrial appendage. In some cases, deploying the pacing device can include placing the sheath parallel to a His bundle of the heart, deploying a lead at an angle from the sheath, and securing at least one of a hook or a screw around a crista supraventricularis of the heart. In some cases, deploying the pacing device can include placing a ring-type pacing device through a partial septum of the heart between a right atrial appendage and a right ventricular outflow tract, and securing the ring via a knot. In some cases, the method can include stimulating the heart with the electrode on the sheath. In some cases, the electrode on the sheath can stimulate the heart when damage is done to the conductive system. In some cases, the pacing device can be collapsible for deployment via the sheath and can be self-expandable upon emergence from the sheath. In some cases, the pacing device can be collapsible for deployment via the sheath and can be actively expanded via a ratchet.

Particular embodiments of the subject matter described in this document can be implemented to realize one or more of the following advantages. First, the designs provided herein facilitate stable, reliable anchoring of electrodes in relation to the myocardium. Second, in some cases the devices provided herein facilitate atrioventricular pacing using a single device implanted in a single location. Third, while placing conventional leads in a thin septum/membrane has been known to cause defects, the systems and methods provided herein create an opening in a controlled manner and then seals the opening. Fourth, the systems and methods provided herein can provide stimulation without causing perforation of the septum. Fifth, the devices and methods provided herein facilitate pacing in specific desirable conduction system areas. Sixth, the device and methods herein facilitate normal and synchronous contraction of the ventricles. Seventh, in some cases the devices and methods provided herein allow for essentially painless cardiac defibrillation. In some embodiments, various heart conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Pulse generation which causes contraction of the selected chamber is termed "capture." Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF DRAWINGS

Like reference numbers represent corresponding parts throughout.

DETAILED DESCRIPTION

This document describes methods and materials for improving artificial cardiac pacing and/or resynchronization. For example, this document describes methods and devices for artificial cardiac pacing and/or resynchronization by stimulating the His bundle.

Most conventional pacemakers have two parts. One part is the generator containing a battery and the electrical circuitry to control the heartbeat. Another part are one or more leads. Leads are wires that connect the heart to the generator and carry the electrical signals to and from the heart. The leads detect the heart's rhythm contractions and send corresponding signals to the controller of the generator. Also, the leads carry the pacing pulses from the generator to the myocardium.

The methods and devices described herein can provide the benefits of providing secure placement of a pacing device. In some embodiments, the methods and devices described herein can provide stimulation of the conduction system without puncturing the septum.

Figure 1:
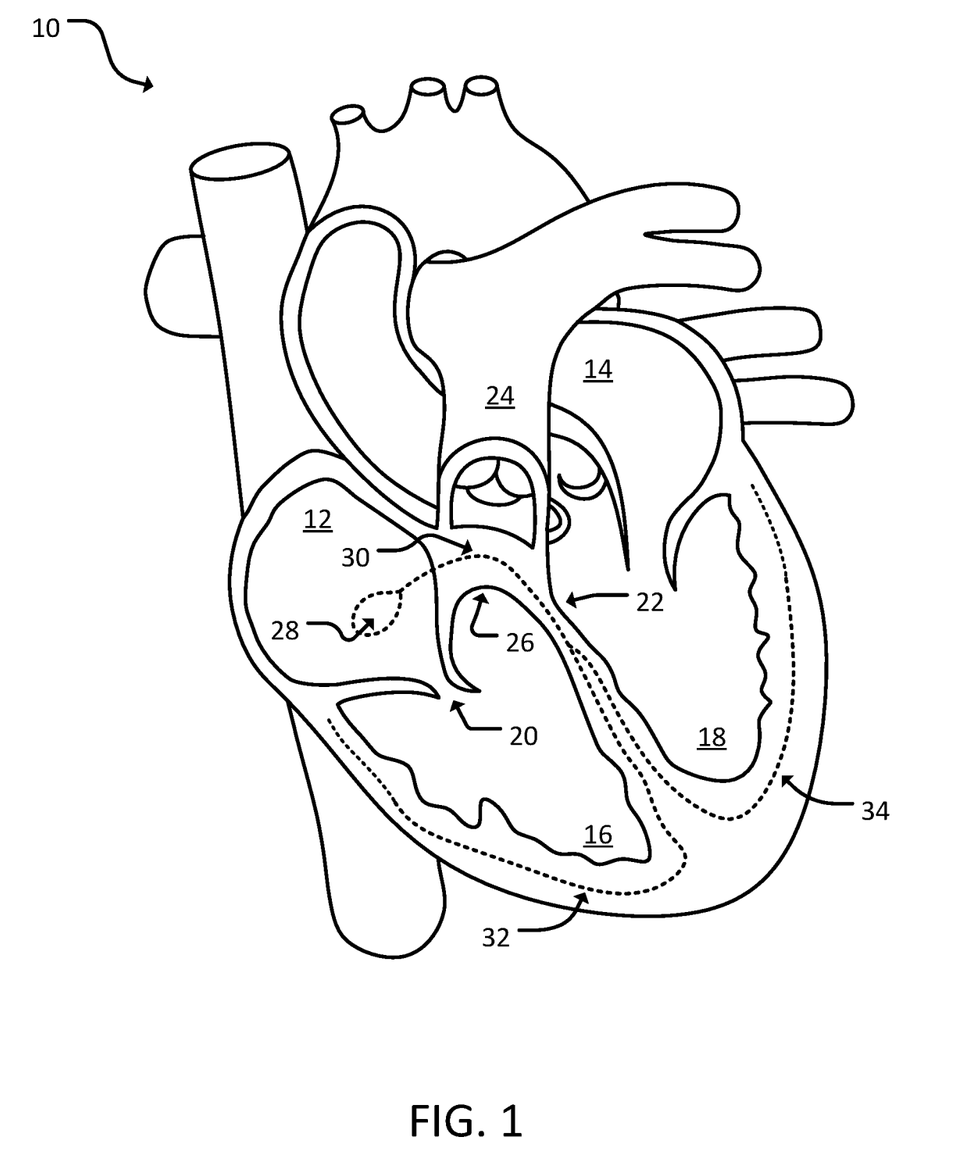
FIG. 1 is a schematic cross-sectional view of a human heart.

Referring to FIG. 1, a human heart 10 can include a right atrium 12, a left atrium 14, a right ventricle 16 and a left ventricle 18.

Between the right atrium 12 and the right ventricle 16 can be a tricuspid valve 20 to facilitate blood flow into the right ventricle 16 from the right atrium 12, and can prevent blood flow into the right atrium 12 from the right ventricle 16. Between the right ventricle 16 and the left ventricle 18 can be a membranous septum 22 that can separate the ventricles 16 and 18. Blood leaving the right ventricle 16 can exit via the right ventricular outflow tract 24. Heart 10 can include a ridge between the right ventricle 16 and an opening of the right ventricular outflow tract 24, known as the crista supraventricularis 26. Heart 10 can also include a conductive system that can cause heart 10 to pump. The conductive system can include an atrioventricular node 28 (AV node) that is a group of specialized cardiac muscle fibers located at the center of the heart, in the floor of the right atrium, between the atria and ventricles. The AV node 28 can lead to a His bundle 30 which transmits impulses from the AV node 28, located at the inferior end of the interatrial septum, to the ventricles 16 and 18 of the heart 10. In some cases, the pulses are transmitted from the His bundle 30 to a right bundle branch 32 and a left bundle branch 34.

Figure 2:
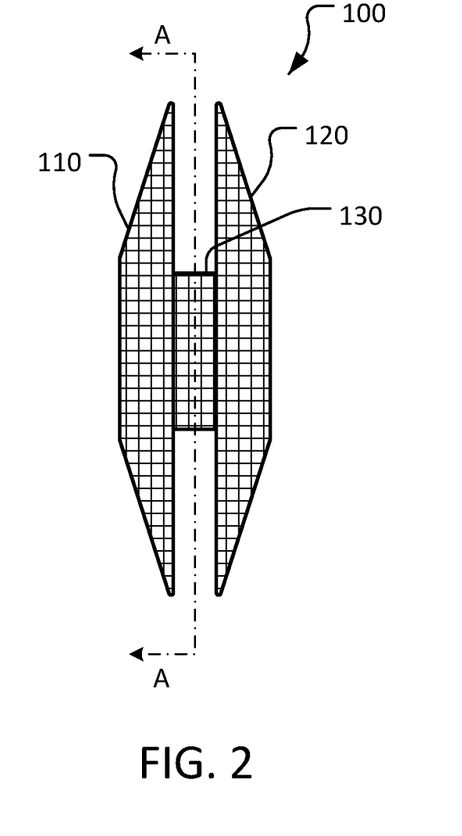
FIG. 2 is a side view of an example cardiac pacing and/or resynchronization electrode-carrying device, in accordance with some embodiments provided herein.
Figure 3:
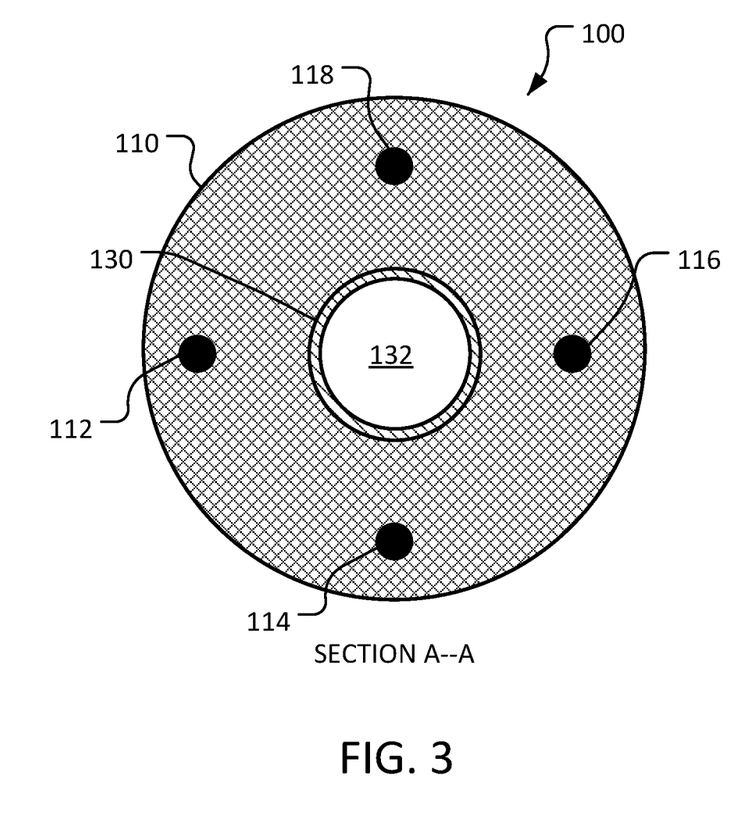
FIG. 3 is a cross-sectional view of the cardiac pacing and/or resynchronization device of FIG. 2.

Referring to FIGS. 2 and 3, an example cardiac pacing and/or resynchronization electrode-carrying cardiac device 100 (hereinafter referred to as "pacing device 100") can be adapted for use in multiple different manners, as described herein. Pacing device 100 includes a first flange portion 110, a second flange portion 120, and a central connecting portion 130. In some cases, portions 110, 120, and 130 are integrally constructed. In some cases, portions 110, 120, and 130 are initially constructed separately and then joined together.

Pacing device 100 is configured for deployment in a minimally-invasive manner. That is, pacing device 100 is diametrically collapsible so that pacing device 100 can be deployed in vivo from a lumen of a low-profile catheter/sheath. Pacing device 100 is shown in its expanded configuration. That is, in some embodiments pacing device 100 will self-expand to the approximate shape shown when relieved from the diametric constraints of a catheter/sheath. Pacing device 100 may become elongated when diametrically collapsed to its low-profile configuration. In some cases, pacing device 100 can be expanded using a ratcheting or other device to deploy the pacing device 100.

In some embodiments, pacing device 100 is made of a framework of one or more elongate members (e.g., wires, struts, and the like). For example, in some embodiments pacing device 100 is made of one or more metallic wires that are braided or woven and then shape-set into the configuration shown. In another example, in some embodiments pacing device 100 is made of a cut-tube of material that is then expanded and shape-set into the configuration shown. In some embodiments, a metal such as Nitinol or stainless steel is used for the framework of pacing device 100. In some embodiments, one or more radiopaque (RO) markers may be included on various locations of the pacing device 100.

Pacing device 100 is compliant, elastic, and flexible so as to conform to the sometimes irregular topography of the tissue that it may be in contact with. Moreover, pacing device 100 is designed to maintain robust tissue contact in spite of the dynamic tissue topography associated with the cardiac cycle.

In some embodiments, pacing device 100 include features directed to enhancing migration resistance such as, but not limited to, macro anchor features (e.g., prongs, hooks, barbs, atraumatic probes, spikes, etc.) or micro anchor features (e.g., a grouping of small protrusions, surface texturing, etc.). One or more mechanical features such as hooks, rings, lassos, tethers, eyelets, and the like can be included on pacing device 100 to facilitate deployment, repositioning, and/or retrieval of pacing device 100.

In some embodiments, a covering material may be included on portions of pacing device 100. Such a covering material may be made of materials including, but not limited to, PTFE, ePTFE, DACRON, and the like. In some cases, the covering material may enhance the occlusive properties of pacing device 100. In some cases, the covering material may be treated to enhance tissue growth, and promote encapsulation and endothelialization of tissue to encourage anatomical closure of a tissue aperture. In some embodiments, the covering can be modified by one or more chemical or physical processes that enhance certain physical properties of the covering. For example, a hydrophilic coating may be applied to the covering to improve the wettability and echo translucency of the covering. In some embodiments, the covering may be modified with chemical moieties that promote one or more of endothelial cell attachment, endothelial cell migration, endothelial cell proliferation, and resistance to thrombosis. In some embodiments, the covering may be modified with covalently attached heparin or impregnated with one or more drug substances that are released in situ to promote wound healing or reduce tissue inflammation. In some embodiments, the drug may be a corticosteroid, a human growth factor, an anti-mitotic agent, an antithrombotic agent, or dexamethasone sodium phosphate.

Pacing device 100 can include one or more pacing electrodes and/or resynchronization coils. In the depicted example embodiment, first flange portion 110 includes four electrodes 112, 114, 116, and 118. As described further below, electrodes 112, 114, 116, and 118 are disposed on the tissue-contacting surface of first flange portion 110 that is inward-facing and that faces second flange portion 120. In some embodiments, electrodes are included only on one portion (either on first flange portion 110 or second flange portion 120) of pacing device 100. In some embodiments, electrodes are included on both portions (on first flange portion 110 and on second flange portion 120) of pacing device 100. Any number of electrodes can be included.

It should be understood that any configuration of a wide variety of possible electrode/coil configurations can be used for pacing device 100, and all such configurations are within the scope of this disclosure. For example, in some embodiments pacing device 100 is configured as a unipolar pacing device. That is, in some embodiments the one or more electrodes of pacing device 100 are cathode(s) electrode(s), and a remotely implanted pulse generator module acts as an anode electrode. In some embodiments, pacing device 100 is configured as a bipolar device. That is, in some embodiments one or more electrodes on one portion of the device (either on first flange portion 110 or second flange portion 120) are cathode(s) and one or more electrodes on the opposite portion of the device are anode(s).

The pulse generation and other control aspects for operating pacing device 100 can originate from various devices and by various technical manners. Any and all such different iterations are within the scope of this disclosure. For example, in some embodiments pacing device 100 is connected via one or more leads to a remotely implanted pulse generator/controller. In some embodiments, pacing device 100 is a wireless pacing device. As a wireless pacing device, pacing device 100 can utilize active RF technology, passive RF technology, or technology by which both pacing device 100 and a remote generator/controller can transmit and receive communications.

In some embodiments, pacing device 100 is fully self-contained. That is, in some embodiments the componentry of a generator/controller can be integrally contained in pacing device 100. For example, in some embodiments pacing device 100 includes an interior space 132 defined by central connecting portion 130 that can house such componentry of a generator/controller.

In some embodiments, pacing device 100 is configured only for cardiac pacing. In some embodiments, pacing device 100 is configured for performance of resynchronization only. In some embodiments, pacing device 100 is configured for both cardiac pacing and resynchronization.

It is also envisioned that a pacing device with the two-part characteristics of pacing device 100 can be used to approximate cardiac structures for pacing and/or resynchronization purposes. For example, in one such exemplary implementation a first portion of the clamshell-like structure can be secured to/against the crista supraventricularis and the second portion can be secured to/against the right atrial appendage. In some implementations, no cardiac structures are punctured, while the implementation helps facilitate multi-site pacing of structure(s) not easy to otherwise pace.

It should be understood that one or more features from a particular embodiment described herein can be combined with one or more features from one or more other embodiments described herein. Hence, all such possible hybrid designs are envisioned within the scope of this disclosure.

Another design iteration that can be incorporated in any of the pacing device embodiments described herein is to make the devices of two materials (e.g., could be two types of nitinol). The first type of material (which, for example, could be near a septal puncture site and/or distally on the circumflex) would be a softer material that is less traumatic, and would not have the electrode components which would necessarily add stiffness. Such a soft material would serve as something as a buttress and hemostatic mechanism while the stiffer portion that includes electrode components will allow for sensing in the pacing and/or defibrillation while maintaining stability and contact. Another design variation can include deployable buttresses or "skirts" that can be activated by an external magnet or an internal deployment device that would be separate from what is left behind, in case bleeding or lack of stability is noted after implant.

Figure 4:
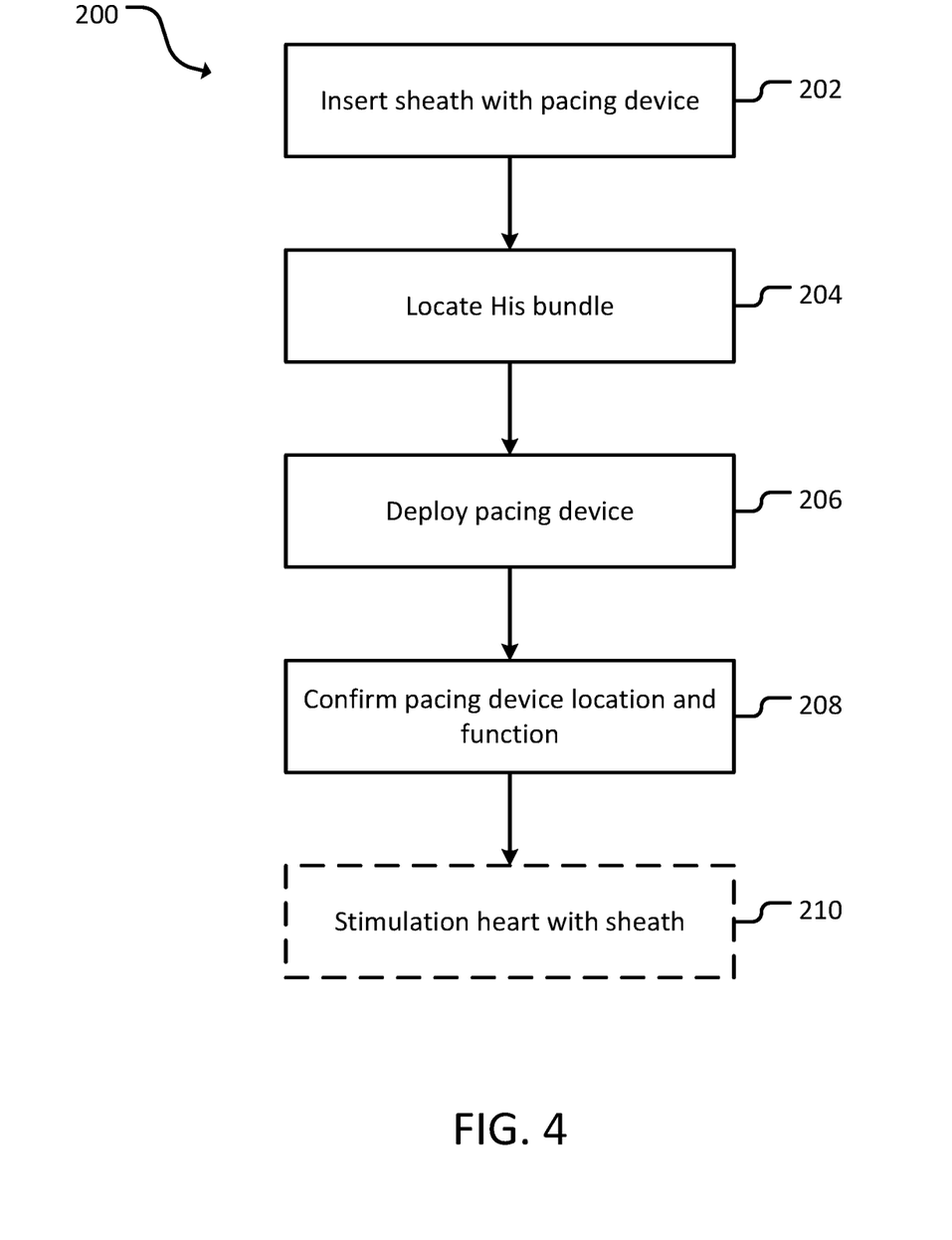
FIG. 4 is a flow chart of a method of implanting a cardiac pacing and/or resynchronization electrode-carrying device, in accordance with some embodiments provided herein.

Referring to FIG. 4, a method of implanting a cardiac pacing and/or resynchronization electrode-carrying device (e.g., pacing device 100) can include inserting a sheath with a pacing device at 202, locating the His bundle at 204, deploying a pacing device at 206, and confirming pacing device location and function at 208.

The operation of inserting a sheath with a pacing device at 202 can include, but is not limited to, inserting through the right atrial appendage and into the right ventricular outflow tract 24. This implementation can provide the capability of atrioventricular pacing without crossing the tricuspid valve 20. In some cases, the outflow tract 24 can produce more synchronous biventricular pacing than other sites.

In some cases, the operation of inserting a sheath with a pacing device 202 can include using a trans-catheter device that facilitates entry of a transseptal-like needle via the right atrial appendage into the right outflow tract 24. In some cases, a small wire can be passed from the right outflow tract 24 into the right atrial appendage. A small wire can be passed from the right outflow tract 24 into the right atrial appendage. For guidance, an expandable or flat deflectable component with or without magnet aid in the right atrial appendage can be used. Such a device can maximize apposition to the right ventricular outflow tract 24 while passing the wire and deploying a device. This technique for deploying a pacing device (e.g., pacing device 100) into the right ventricular outflow tract 24 can in some cases decrease the potential for bleeding into the pericardial space.

In some cases, a pacing device can be implanted using various minimally invasive or surgical techniques. For example, in some cases, a pacing device can be placed using an endocardial approach via vascular access. In such a case, femoral veins, subclavian veins, internal jugular veins, and the like, can be used for transvenous access. In some cases, an epicardial approach can be used to place a pacing device. In such a case, subxiphoid or intercostal accesses can be used for example. In some cases, a pacing device can be implanted using an open chest surgical technique. Moreover, in some cases, a guidewire, along with a puncture needle, is inserted into the vasculature, internally snared, and then pulled out of the patient so that both ends of the guidewire are controlled using a counter-traction technique. In such a case, a pacing device can then be implanted using either an inside out technique, or an outside in technique.

The process of locating the His bundle 30 at operation 204 can include, but is not limited to, moving the sheath until the sheath is parallel to the His bundle 30. In some cases, the sheath can include multiple electrodes. The electrodes on the sheath can record His bundle activity to confirm the sheath is located near the His bundle 30. In some cases, the sheath is held against the His bundle 30 until placement of the pacing device is complete. In some cases, templates of the His bundle recording and far-field as well as near-field ventricular myocardial recordings are programmed into a delivery device, such that a sheath perpendicular to the tricuspid annulus and parallel to the His bundle 30 is deployed in the commissure between the anterior and septal leaflet of the tricuspid valve 20.

Deploying a pacing device at operation 206 can include, but is not limited to, deploying the pacing device once the appropriate template is matched, thus recognizing the location of the His bundle 30. In some cases, the pacing device can be deployed through an opening of the sheath. In some cases, the opening of the sheath can be located between electrodes of the sheath. In some cases, the lead can be deployed out of the sheath at an angle.

In some cases, an intramyocardial clamshell pacing device can be placed just distal to the membranous septum 22. In some cases, all surfaces of the clamshell are capable of stimulation. In some cases, a distal shell of the clamshell can be placed within the myocardium and the proximal shell of the clamshell can be placed on the right ventricular aspect. In some cases, the distal intramyocardial clamshell pacing device is deployed in a compact manner and expands in natural intramycaridal layers. In some cases, this expansion can be done passively. In some cases, this expansion can be done actively with a ratchet-type of deployment system. In some cases, a connecting piece between the clamshells can be insulated to allow bipolar stimulation. In some cases, the clamshell device can be attached to a standard lead. In some cases, the clamshell device can include a battery and other systems to provide for leadless pacing. In some cases, the clamshell can be asymmetrical. For example, a portion of the clamshell located in the right ventricular side may be larger to house the battery. In some cases, the clamshell can be a dipole. In some cases, the clamshell can capture multiple portion so of the heart. In some cases, the clamshell device can provide stimulation of the atrium and/or ventricles in case damage occurs to the His bundle 30.

In some cases, deploying a pacing device at 206 can include a multi-electrode clamp-like design. In some cases, the clamp-like design can be used such that a distal portion is distal to the crista supraventricularis 26 and just into the proximal right ventricular outflow tract 24 (FIG. 1). In some cases, the proximal portion of the clamp-like design can be located through the penetrating bundle of His 30 and the transition zone and can be placed in a clamp-like manner just into the right atrial appendage. In some cases, the clamp can passively tighten (e.g., shape memory returning to an original shape). In some cases, the clamp can be actively tightened with a ratchet type device. In some cases, the clamp can include multiple electrodes that traverse the His bundle 30 and other conduction systems. In this case, the clamp can allow stimulation of multiple sites so as to increase the source-sink mismatch and potentially overcome distal bundle-branch block. In this case, there can be flexibility to find an optimum pacing threshold among different portions of the His bundle 30.

In some cases, deploying a pacing device at operation 206 can include a clamp device that has a first portion that can be located on the crista supraventricularis 26 and a second portion that can be located in a shelf of the tricuspid area 20 of the membrane, with the septum in between. In some cases, the clamp device can cross the shelf and curve back. In some cases, the clamp device can be capable of stimulating the His bundle 30, the atrium 12 and/or 14, and the ventricle 16 and/or 18. In some cases, the His bundle 30, the atrium 12 and/or 14, and the ventricle 16 and/or 18 can be stimulated with a single stimulation.

In some cases, deploying a pacing device at 206 can include placing a pacing device such that electrodes are placed distal to the crista supraventricularis 26 on the right ventricular outflow tract 24 posteriorly so as to capture and pace left ventricular myocardium on the outflow tract septum for myocardial resynchronization in addition to His bundle 30 pacing. In some cases, the electrodes located on the His bundle 30 can, over time, give rise to His bundle 30 damage or the patient can develop conduction block distal to the His bundle 30 due to increasing age or disease. In some cases, the atriobiventricular pacing can continue with resynchronization and hemodynamic benefits.

In some cases, deploying a pacing device at 206 can include a ring or clamshell type device that is inserted through the partial septum between the right atrial appendage and the right ventricular outflow tract 24. In some cases, the puncture through the partial septum is purposeful and allows a snaring device to be used to advance a knot, securing the device in place. In some cases, the ring or clamshell device can include elements to prevent bleeding. In some cases, the ring or clamshell device can include a series of electrodes capable of atrial pacing, atrial sensing, conduction system sensing, conduction system pacing, as well as ventricular sensing and pacing. In some cases, the pacing device can have multiple electrodes. In some cases, when the electrodes sense a loss of capture, an electrode configuration can change and/or an intensity can be increased. In some cases, the device can be C-shaped and sits on the ventricle at the end of the right atrial appendage. In some cases, the device can be O-shaped and entered into the ventricle from the right atrial appendage. In some cases, the ring type device can surround the aortic annulus. In some cases, the ring type device can include pressure sensors to monitor aortic pulsations and/or aortic annulus excursion. In some cases, aortic pulsations and/or aortic annulus excursion can be a surrogate for cardiac output, blood pressure, and/or stroke volume. In some cases, the sensors can be standalone sensors or integrated into a pacing output algorithm to optimize biventricular and His bundle pacing. In some cases, the optimized pacing can be based on stroke volume, blood pressure, etc. In some cases, the clamp design can provide various pressures around or near the aortic annulus and valve and can be manipulated and calibrated to minimize aortic regurgitation, aortic annular dilation, and other disease of the aortic valve.

In some cases, deploying a pacing device at operation 206 can include a helical screw-in type system. Such a helical screw-in type system can be attached so that the system is parallel to the His bundle 30. In some cases, the helical screw-in type system can be hooked around the crista supraventricularis 26. In some cases, the system can include hooks parallel to the distal element of the lead around the crista supraventricularis 26 that can provide stability. The helical screw-in type system may provide sensing and pacing of the conductive system. In some cases, the electrodes can be advanced into the His bundle 30 and related structures without the need to move the delivery sheath that constantly monitors and senses the conduction system signals. Electrodes may be comprised as hooks or screws in some cases.

Confirming a pacing device location and function at operation 208 can include using the sheath to sense capture of the His bundle 30. If capture is not sensed, the pacing device can be moved. Alternatively, or additionally, if capture is not sensed, an electrode configuration can be modified. In some cases, if capture is sensed, the sheath can be removed with the pacing device being left for continual stimulation.

Some iterations of the device have no elements that penetrate the conductive system, thereby reducing the risks of, or preventing damage of, the conductive system. In some cases, the penetration of the conductive system is done at multiple sites such that one damaged element can immediately be bypassed by stimulating an electrode distal to that element of the conduction system with a distal electrode hooked around the crista supraventricularis, without system penetration.

In some cases, implanting a cardiac pacing device can include stimulating the heart with the sheath at optional operation 210. For example, if the His bundle 30 or other conductive system becomes damaged, the sheath can stimulate the heart to prevent loss of stimulation.

In some cases, due to the proximity of the myocardium in this region to autonomic neural ganglia in the peri-aortic and pen-pulmonary annulus that govern vascular tone in the systemic and pulmonary circulation, the pacing devices can be used for high output stimulation. In some cases, the delivery of such high output stimulation can include the use of algorithms that can increase or decrease stimulation as needed based on systemic and/or pulmonary blood pressures. In some cases, pacing can treat some forms of fainting/syncope, hypertension/high blood pressure, and/or pulmonary hypotension.

While the devices and methods provided herein are described primarily in the context of pacing, it should be understood that resynchronization can additionally or alternatively be performed in an analogous manner, and that the scope of this disclosure includes such subject matter.

In some embodiments, the devices provided herein are well-suited to providing specific conduction system pacing, i.e., in specific desirable cardiac conduction system areas. For example, as described further below, some embodiments provided herein provide pacing in specific desirable conduction system areas such as, but not limited to the His bundle, the penetrating bundle of His, the proximal conduction system, to provide a few examples. In some cases, such an implementation would facilitate specific conduction system capture and sensing in addition to atrial and ventricular pacing.

In some embodiments, the devices provided herein are not limited to pacing the His bundle, but can also pace the AV node, the right bundle branch, or other conductive systems.

In some embodiments, the devices provided herein are configured to be retrievable. For example, in some embodiments the devices provided herein can be recaptured into the lumen of a catheter/sheath and removed from the patient endovascularly. In some embodiments, the devices provided herein can be retrieved using a subcutaneous retrieval technique.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. A method of treating a human heart, wherein the method comprises:
   inserting a sheath with a pacing device in the heart, wherein the sheath comprises an electrode;
   locating a conductive system of the heart via the electrode on the sheath;
   deploying the pacing device in the heart, wherein the deploying comprises:
      placing a distal portion of the pacing device just distal to a crista supraventricularis of the heart in a proximal right ventricular outflow tract; and
      placing a proximal portion of the pacing device through a His bundle of the heart and is placed in a clamp-like manner into the proximal right atrial appendage; and
   confirming, via the electrode on the sheath, function of the pacing device.

2. The method of claim 1, wherein the pacing device comprises:
   a first flange portion;
   a second flange portion;
   a central portion extending between and connecting the first flange portion and the second flange portion; and
   one or more pacing electrodes exposed on an inward-facing surface of the first flange portion that faces the second flange portion.

3. The method of claim 1, wherein the conductive system is the His bundle of the heart.

4. The method of claim 3, wherein locating the His bundle of the heart comprises recording His bundle activity via the electrode on the sheath.

5. The method of claim 4, wherein templates of the His bundle recording is compared to the His bundle activity recorded via the electrode on the sheath to confirm location of the His bundle.

6. The method of claim 1, wherein the method further comprises stimulating the heart with the electrode on the sheath.

7. The method of claim 6, wherein the electrode on the sheath stimulates the heart when damage is done to the conductive system.

8. The method of claim 1, wherein the pacing device is collapsible for deployment via the sheath and is self-expandable upon emergence from the sheath.

9. The method of claim 1, wherein the pacing device is collapsible for deployment via the sheath and is actively expanded via a ratchet.

10. A method of treating a human heart, wherein the method comprises:
    inserting a sheath with a pacing device in the heart, wherein the sheath comprises an electrode;
    locating a conductive system of the heart via the electrode on the sheath;
    deploying the pacing device in the heart, wherein the deploying comprises:
       placing a ring-type pacing device through a partial septum of the heart between a right atrial appendage and a right ventricular outflow tract; and
       securing the ring via a knot; and
    confirming, via the electrode on the sheath, function of the pacing device.

11. The method of claim 10, wherein the conductive system is a His bundle of the heart.

12. The method of claim 11, wherein locating the His bundle of the heart comprises recording His bundle activity via the electrode on the sheath.

13. The method of claim 12, wherein templates of the His bundle recording is compared to the His bundle activity recorded via the electrode on the sheath to confirm location of the His bundle.

14. The method of claim 10, wherein the method further comprises stimulating the heart with the electrode on the sheath.

15. The method of claim 14, wherein the electrode on the sheath stimulates the heart when damage is done to the conductive system.

16. The method of claim 10, wherein the pacing device is collapsible for deployment via the sheath and is self-expandable upon emergence from the sheath.

17. The method of claim 10, wherein the pacing device is collapsible for deployment via the sheath and is actively expanded via a ratchet.

* * * * *